United States Patent
Milstein et al.

[11] Patent Number: 5,908,928
[45] Date of Patent: Jun. 1, 1999

[54] ALKYL POLYGLYCOSIDE ETHER CARBOXYLATES

[75] Inventors: Norman Milstein, Montgomery, Ohio; Barry A. Salka, Fair Lawn, N.J.

[73] Assignee: Henkel Corporation, Plymouth Meeting, Pa.

[21] Appl. No.: 08/967,079

[22] Filed: Nov. 10, 1997

Related U.S. Application Data

[63] Continuation-in-part of application No. 08/646,546, May 8, 1996, abandoned.

[51] Int. Cl.$^6$ .......................... C07H 15/06; C07H 15/08; C11D 3/22
[52] U.S. Cl. .......................... 536/120; 536/4.1; 536/18.5; 536/18.6; 536/123.1; 536/123.13; 510/108; 510/470
[58] Field of Search ...................... 510/108, 470; 536/18.5, 18.6, 120, 123.1, 123.13, 401

[56] References Cited

U.S. PATENT DOCUMENTS

| | | | |
|---|---|---|---|
| 4,599,188 | 7/1986 | Llenado | 252/174.17 |
| 4,806,275 | 2/1989 | Johnson et al. | 252/554 |
| 5,179,201 | 1/1993 | Oftring et al. | 536/4.1 |
| 5,266,690 | 11/1993 | McCurry, Jr. et al. | 536/18.6 |
| 5,334,756 | 8/1994 | Likibi et al. | 562/565 |
| 5,504,246 | 4/1996 | Likibi et al. | 562/540 |
| 5,545,731 | 8/1996 | Weuthen | 510/119 |
| 5,602,093 | 2/1997 | Haerer et al. | 510/514 |

FOREIGN PATENT DOCUMENTS

| | | |
|---|---|---|
| 70075 | 1/1983 | European Pat. Off. . |
| 70076 | 1/1983 | European Pat. Off. . |
| 0457965 | 11/1991 | European Pat. Off. . |

*Primary Examiner*—Howard C. Lee
*Attorney, Agent, or Firm*—Wayne C. Jaeschke; John E. Drach; Steven J. Trzaska

[57] ABSTRACT

A novel surfactant of formula I:

$$R_1O(R_2O)_b(Z)_aOCH_2COO^-X^+ \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion.

18 Claims, No Drawings ns 5,908,928

ALKYL POLYGLYCOSIDE ETHER CARBOXYLATES

This application is a continuation, of application Ser. No. 08/646,546 filed on May 8, 1996, now abandoned.

FIELD OF THE INVENTION

The present invention generally relates to alkyl polyglycoside ether carboxylates, their preparation, and to their use as surfactants.

BACKGROUND OF THE INVENTION

It is known that various surfactants have been found to be useful in cleaning compositions, such as shower gels, shampoos, and light duty detergents such as dish washing detergents. Un these types of compositions, good foamability is a prerequisite. The most widely used surfactants in these types of compositions are anionic surfactants such as alkyl sulfates, alkyl ether sulfates, sulfonates, sulfosuccinates and sarcosinates.

Although the use of anionic surfactants in these compositions permits the attainment of desirable properties, including good foamability, the degree of foam stability leaves much to be desired. Foam stability relates to the ability of the foam, once formed, to remain intact for extended periods of time, thus enhancing the cleaning performance of the surfactant compositions.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. For example, a mixture of more costly surfactants such as amine oxides, betaines and alkanolamides which provide good foamability by themselves, with less expensive surfactants which provide poorer foamability will result in the formulation of a cleaning composition having an intermediate degree of foamability and poor foam stability.

Alkyl polyglycosides are used as nonionic surfactants and are distinguished from other nonionic surfactants by their excellent detergent properties and high ecotoxicological compatibility. For this reason, this class of nonionic surfactants is acquiring increasing significance. They are generally used in liquid formulations, for example dishwashing detergents and hair shampoos. However, because of there increased desirability as surface active agents, there use as surfactants in many other types of products is growing rapidly.

While the use of mixtures of anionic and nonionic surfactants in most cases serves to further the objectives of both classes of surfactants, it would be much more desirable, and significantly less costly to employ, a single compound which would exhibit the favorable properties which are indigenous to both anionic and nonionic surfactants.

SUMMARY OF THE INVENTION

The present invention provides a novel surfactant having general formula I:

$$R_1O(R_2O)_b(Z)_aOCH_2COO^-X^+ \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion.

There is also provided a process for making novel surfactants involving:

(a) providing an alkyl polyglycoside having general formula II:

$$R_1O(R_2O)_b(Z)_a \qquad II$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6;

(b) providing a non-aqueous alkali metal compound;

(c) dispersing the alkyl polyglycoside in the nonaqueous alkali metal compound to form a reaction mixture; and (d) adding an acetate derivative to the reaction mixture to form a reaction product.

DESCRIPTION OF THE INVENTION

Other than in the operating examples, or where otherwise indicated, all numbers expressing quantities of ingredients or reaction conditions are to be understood as being modified in all instances by the term "about".

The alkyl polyglycosides which can be used in the compositions according to the invention have the general formula II:

$$R_1O(R_2O)_b(Z)_a \qquad II$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkyl polyglycoside in which the alkyl group contains 8 to 10 carbon atoms and has an average degree of polymerization of 1.7.

2. GLUCOPON® 425 Surfactant—an alkyl polyglycoside in which the alkyl group contains 8 to 16 carbon atoms and has an average degree of polymerization of 1.55.

3. GLUCOPON® 625 Surfactant—an alkyl polyglycoside in which the alkyl groups contain 12 to 16 carbon atoms and have an average degree of polymerization of 1.6.

4. APG® 325 Surfactant—an alkyl polyglycoside in which the alkyl groups contain 9 to 11 carbon atoms and have an average degree of polymerization of 1.6.

5. GLUCOPON® 600 Surfactant—an alkyl polyglycoside in which the alkyl groups contain 12 to 16 carbon atoms and have an average degree of polymerization of 1.4.

6. PLANTAREN® 2000 Surfactant—a $C_{8-16}$ alkyl polyglycoside in which the alkyl group contains 8 to 16 carbon atoms and has an average degree of polymerization of 1.5.

7. PLANTAREN® 1300 Surfactant—a $C_{12-16}$ alkyl polyglycoside in which the alkyl groups contain 12 to 16 carbon atoms and have an average degree of polymerization of 1.6.

8. PLANTAREN® 1200 Surfactant—a $C_{12-16}$ alkylpolysaccharide in which the alkyl groups contain 12 to 16 carbon atoms and have an average degree of polymerization of 1.4.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of aikyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked aikyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

A particularly preferred alkyl polyglycoside of formula II is one wherein $R_1$ is a monovalent organic radical having from 12 to 16 carbon atoms, b is zero, and a is a number having a value of about 1.4.

According to one aspect of the invention, there is provided a novel surfactant having general formula I:

$$R_1O(R_2O)_b(Z)_aOCH_2COO^-X^+ \quad \text{I}$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion.

These novel surfactants possess both anionic and nonionic properties. They provide superior levels of stable foam and act as viscosity builders when used in various types of detergent compositions.

In a particularly preferred embodiment of the novel surfactant of formula I, $R_1$ is a monovalent organic radical having from 12 to 16 carbon atoms, b is zero, and a is a number having a value of about 1.4.

Another aspect of the present invention provides a process for making the above-disclosed novel surfactants. According to this aspect of the invention, the alkyl polyglycosides of formula II are etherified by reaction with a chloro acetate derivative such as, for example, sodium monochloroacetate. This reaction is carried out in a non-aqueous medium in the presence of alkali metal ions, preferably potassium or sodium ions. The alkali metal compound is preferably employed in the form of an oxide such as, for example, sodium ethoxide, sodium hydroxide or potassium tert-butoxide.

In a preferred embodiment of the invention, about 1 mole of alkyl polyglycoside is first reacted with from about 1 to about 2 moles, and most preferably about 1 mole of alkali metal oxide to form a reaction mixture. This reaction is preferably carried out at a temperature ranging from about 70 to about 90° C., and most preferably about 80° C., and at a pH ranging from about 10 to about 14, and most preferably about 12.

Once the reaction mixture is formed, from about 1 to about 2 moles, and preferably about 1 mole of a chloroacetate derivative is added to the reaction mixture. Examples of suitable chloroacetate derivatives include, but are not limited to, sodium monochloroacetate and ethyl chloroacetate. In a particularly preferred embodiment, the chloroacetate derivative is sodium monochloroacetate.

The chloroacetate derivative is added to the reaction mixture at a temperature ranging from about 60 to about 70° C., and a pH ranging from about 12 to about 14.

A procedure for making the novel surfactant is as follows. An alkyl polyglycoside is mixed with an organic reagent such as, for example, xylene or toluene, and subsequently heated in order to azeotropically remove any water contained in the alkyl polyglycoside, thus forming a mixture of anhydrous alkyl polyglycoside and solvent. This mixture is then heated to a temperature of about 70° C. at which time an alkali metal compound is added. A solvent such as, for example, ethanol may be added to the mixture in order to liquify the mixture if needed. The chloroacetate derivative is then added to the reaction mixture, thereby etherifying the alkyl polyglycoside so as to form the novel surfactant of formula I.

According to another aspect of the invention, there is provided a cleaning composition containing from about 20 to about 35% by weight, and preferably from about 25 to about 30% by weight of the novel surfactant of formula I, based on the weight of cleaning composition. The formulation of cleaning compositions may vary widely. It is well known that detergent and cleaning compositions contain surfactants and, in most cases, builders. While various surfactants, builders and additives may be employed in combination with the novel surfactant of formula I, the basis of this aspect of the invention is the presence of the surfactant of formula I in a cleaning composition, in the above-disclosed amounts.

The following example is illustrative of the process and composition of the present invention and will be useful to one of ordinary skill in the art in practicing the invention. However, the invention is in no way limited by these examples.

EXAMPLE 1

A mixture of 650 grams (one mole) of a $C_{12-16}$ alkyl polyglycoside having an average degree of polymerization of 1.4 and 700 ml of toluene were heated in order to azeotropically distill any water present in the alkyl polyglycoside, using a Dean Stark trap. The temperature of the mixture rose from 85° C. to 110° C. The distillation required about 4 hours. The dry alkyl polyglycoside was clearly soluble in the toluene at room temperature. To this mixture, 485 grams (one mole) of ethanolic sodium hydroxide was added, with agitation. When the addition was complete, the reaction mixture was heated to about 60° C. for about 1 hour, at which time 116.5 grams (one mole) of sodium monochloroacetate was added, with stirring, and was refluxed for about 5 hours. Water was then added in 200 ml increments while distilling, in 200 ml increments, the ternary azeotrope (toluene/ethanol/water) until the pot temperature reached about 100° C. and only water remained in the product. This required about 8 hours. The distillate came off as two layers: the top layer being rich in toluene, and the bottom layer being rich in water. The top layer was used to azeotropically dry the next batch of alkyl polyglycoside starting material, the distillate initially consisting of the ternary azeotrope, toluene/ethanol/water, and finishing as the binary azeotrope, toluene/water. Wet analysis data performed on the residue is found in Table I below.

TABLE I

| Appearance at 25° C. | clear liquid |
|---|---|
| Color, Gardner | 4 |
| Solids, % | 32.8 |
| pH (5% solids) | 9.0 |

What is claimed is:

1. A process for making a surfactant comprising:
   (a) providing an alkyl polyglycoside having general formula II:

$$R_1O(R_2O)_b(Z)_a \qquad \text{II}$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6;

(b) providing a non-aqueous alkali metal compound;
   (c) dispersing the alkyl polyglycoside in the nonaqueous alkali metal compound to form a reaction mixture; and
   (d) adding a chloroacetate derivative to the reaction mixture to form the surfactant.

2. The process of claim 1 wherein in formula II $R_1$ is a monovalent organic radical having from 12 to 16 carbon atoms, b is zero, and a is a number having a value of about 1.4.

3. The process of claim 1 wherein the alkali metal compound is selected from the group consisting of sodium ethoxide, sodium hydroxide, potassium tert-butoxide and mixtures thereof.

4. The process of claim 1 wherein the chloroacetate derivative is selected from the group consisting of sodium monochloroacetate, ethyl chloroacetate and mixtures thereof.

5. The process of claims 4 wherein the chloroacetate derivative is sodium monochloroacetate.

6. The product of the process of claim 1.
7. The product of the process of claim 2.
8. The product of the process of claim 3.
9. The product of the process of claim 4.
10. The product of the process of claim 5.
11. A cleaning composition comprising from about 20 to about 35% by weight, based on the weight of the cleaning composition, of a surfactant having formula I:

$$R_1O(R_2O)_b(Z)_aOCH_2COO^-X^+ \qquad \text{I}$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6; and X is an alkali metal ion.

12. The process of claim 1 wherein about 1 mole of the alkyl polyglycoside of formula II is combined with about 1 mole of the non-aqueous alkali metal compound to form the reaction mixture.

13. The process of claim 12 wherein about 1 mole of the chloroacetate derivative is added to the reaction mixture to form the novel surfactant.

14. The process of claim 1 wherein step (c) is performed at a temperature of about 70° C.

15. The product of the process of claim 12.
16. The product of the process of claim 13.
17. The product of the process of claim 14.

18. The composition of claim 11 wherein the surfactant is present in the composition in an amount of from about 25 to about 30% by weight, based on the weight of the composition.

* * * * *